United States Patent
Oshiki et al.

(10) Patent No.: US 8,047,989 B2
(45) Date of Patent: Nov. 1, 2011

(54) MEDICAL IMAGING DIAGNOSIS APPARATUS AND MEDICAL IMAGING DIAGNOSIS METHOD

(75) Inventors: Mitsuhiro Oshiki, Tokyo (JP); Ryuichi Shinomura, Saitama (JP)

(73) Assignee: Hitachi Medical Corporation, Tokyo (JP)

( * ) Notice: Subject to any disclaimer, the term of this patent is extended or adjusted under 35 U.S.C. 154(b) by 627 days.

(21) Appl. No.: 10/593,072

(22) PCT Filed: Mar. 10, 2005

(86) PCT No.: PCT/JP2005/004173
§ 371 (c)(1),
(2), (4) Date: Sep. 15, 2006

(87) PCT Pub. No.: WO2005/087111
PCT Pub. Date: Sep. 22, 2005

(65) Prior Publication Data
US 2007/0149877 A1    Jun. 28, 2007

(30) Foreign Application Priority Data

Mar. 15, 2004   (JP) ................................. 2004-073300
Oct. 14, 2004   (JP) ................................. 2004-300334

(51) Int. Cl.
*A61B 8/00*    (2006.01)
(52) U.S. Cl. ........ 600/437; 600/407; 600/454; 600/465; 600/441; 600/479
(58) Field of Classification Search .................. 600/407, 600/437
See application file for complete search history.

(56) References Cited

U.S. PATENT DOCUMENTS 5,353,220 A * 10/1994 Ito et al. ................... 600/437
5,615,680 A * 4/1997 Sano ........................ 600/437
6,132,373 A * 10/2000 Ito et al. ................... 600/437

FOREIGN PATENT DOCUMENTS

| JP | 5-261101    | 10/1993 |
| JP | 11-342132   | 12/1999 |
| JP | 2000-172829 | 6/2000  |
| JP | 2000-271117 | 10/2000 |
| JP | 2003-245280 | 9/2003  |

OTHER PUBLICATIONS

Japanese Office Action, dated Feb. 21, 2011, issued in corresponding Japanese Patent Application No. 2006-510975.

* cited by examiner

*Primary Examiner* — Tse Chen
*Assistant Examiner* — Joel F Brutus
(74) *Attorney, Agent, or Firm* — Antonelli, Terry, Stout & Kraus, LLP.

(57) ABSTRACT

A medical imaging diagnosis apparatus for measuring the composite thickness of the tunica intima and the tunica media of a blood vessel of a subject by acquiring image data on the blood vessel. In order to improve the accuracy of the IMT measurement of the composite thickness, the medical imaging diagnosis apparatus has extracting means for extracting the tunica intima and the tunica externa of the blood vessel on the basis of the brightness information of the image data to measure the composite thickness of the tunica intima and the tunica externa of the vessel in reference to the two extracted regions.

19 Claims, 14 Drawing Sheets

FIG. 4
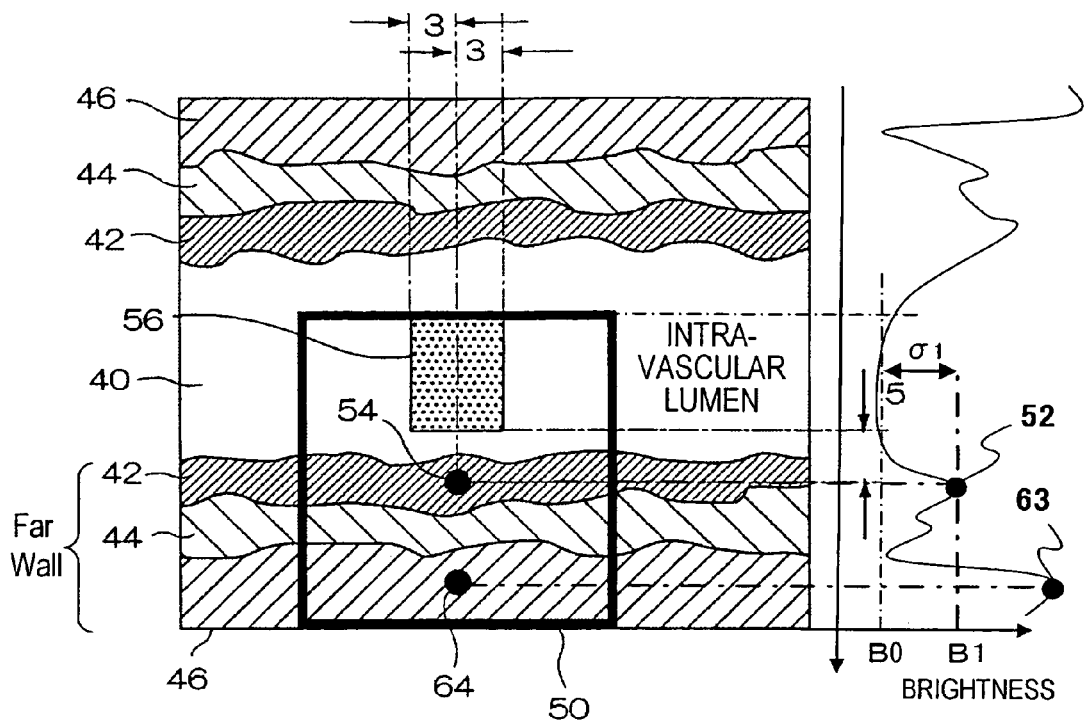
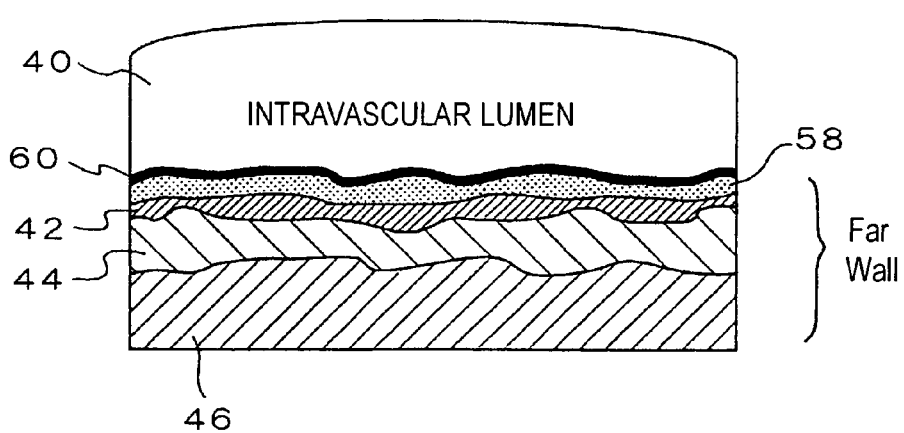

FIG. 6
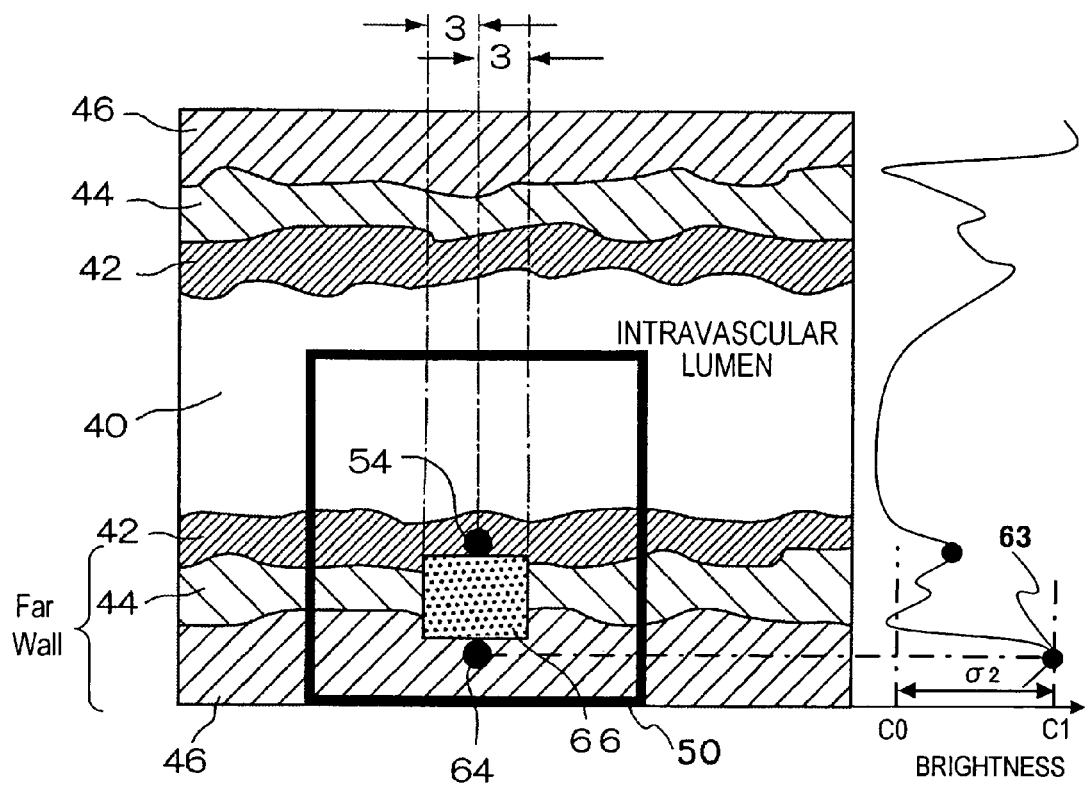
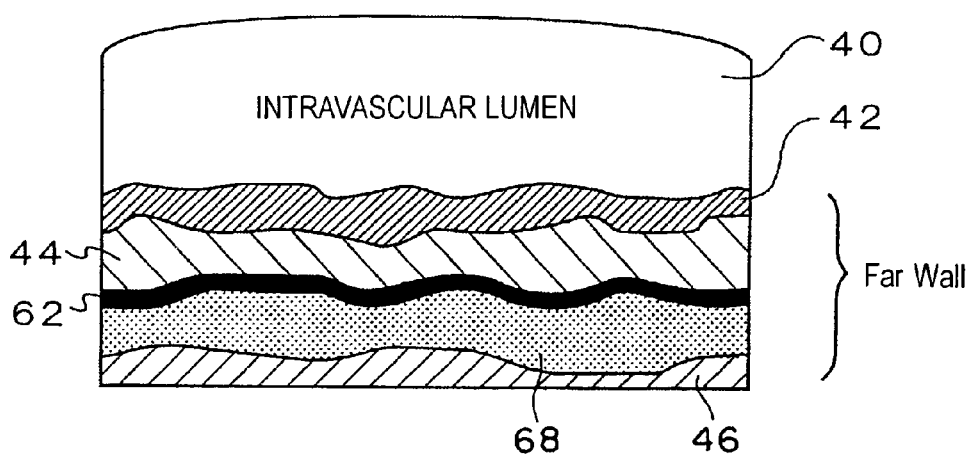

MEDICAL IMAGING DIAGNOSIS APPARATUS AND MEDICAL IMAGING DIAGNOSIS METHOD

TECHNICAL FIELD

The present invention relates to a medical imaging diagnosis device and medical imaging diagnosis method for performing IMT measurement.

BACKGROUND ART

An ultrasound diagnostic apparatus being a kind of medical imaging diagnostic apparatus obtains image data by transmitting/receiving ultrasonic waves between an object being examined via a probe and reconstructing ultrasound images (for example, B-mode images) based on echo signals generated from the object.

In such ultrasound diagnostic apparatus, the measurement of intima media thickness (hereinafter referred to as IMT) of a blood vessel wall is implemented in order to identify arteriosclerosis or cardiovascular diseases at an early stage. A blood vessel wall is formed with a trilaminar structure consisting of tunica intima, tunica media and tunica externa in due order from the lumen side where blood flows. IMT is the sum of the thickness of the tunica intima and the tunica media, in other words the distance from the inner wall of the tunica intima to the inner wall of the tunica media.

In the ultrasound apparatus for measuring IMT, for example, the brightness distribution in the thickness direction of a blood vessel wall of image data in one line is obtained, and the local maximal point having the maximum brightness of the brightness distribution is set as tunica externa reference point A. The second local maximal point that appears from tunica externa reference point A in the lumen side is set as tunica intima reference point B. Then IMT measurement is performed by setting minimum point C that appears in the lumen side from tunica media reference point B as the inner wall of the lumen, as well as setting the midpoint between point D having the minimum brightness of the brightness distribution and tunica externa reference point A as the inner wall of the lumen (refer, for example, to Patent Document 1).
Patent Document 1: JP-A-99-318896

However, with the technique in Patent Document 1, once in a while minimum point C does not appear clearly in the lumen side from the tunica media reference point in the brightness distribution of image data. Also, setting the midpoint between point D and tunica externa reference point A as the inner wall position of the tunica externa is based on empirical rules obtained from factors such as clinical results. Due to the individual variability of objects being examined, there are cases that IMT cannot be measured accurately. Therefore there is a demand for improvement of IMT measurement.

It is the objective of the present invention to provide a medical imaging diagnostic apparatus and method with improved accuracy for the measurement of IMT.

DISCLOSURE OF THE INVENTION

In order to solve the above-mentioned problems, the medical imaging diagnostic apparatus for using with the present invention obtains image data of a blood vessel of an object being examined and measures the composite thickness of a tunica intima and a tunica media of the blood vessel, comprising extraction means for extracting the tunica intima and the tunica media of the blood vessel based on the brightness information of image data, wherein the composite thickness of the tunica intima and the tunica media of the blood vessel is measured based on the two extracted regions.

In concrete terms, it is characterized in comprising:
imaging means for obtaining image data related to a blood vessel;
brightness distribution acquisition means for acquiring the brightness distribution in the thickness direction of a blood vessel wall appearing in the brightness distribution;
setting means for setting, out of the local maximal points which appear in the brightness distribution, the local maximal point of the lumen side as the tunica intima reference point and the local maximal point having the maximum brightness as the tunica externa reference point;
extraction means, with respect to the pixels within the setting region including the tunica intima or the tunica externa, for extracting the pixels wherein the brightness belong to the setting range; and
calculation means for calculating the distance between the boundary of the blood vessel wall side in the region formed by the pixels being extracted based on the tunica intima reference point and the boundary of the lumen side in the region formed by the pixels being extracted based on the tunica externa reference point.

Since the acoustic impedance of the tunica intima is comparatively greater than the acoustic impedance of the lumen of a blood vessel in general, the brightness difference between the pixels of lumen and the pixels of tunica intima turns out to be great. Also, since the acoustic impedance of the tunica externa is comparatively greater than the acoustic impedance of the tunica media of a blood vessel in general, the brightness difference between the pixels of tunica media and the pixels of tunica externa turns out to be great.

Therefore by properly setting the setting range of the brightness of pixels to be extracted, it is possible to extract the pixels corresponding to the lumen or tunica externa. The inner wall of the tunica intima (the boundary of the tuncia intima and the lumen) or the inner wall of the tunica externa (the boundary of the tunica externa and tunica intima) can be detected precisely from the extracted pixel region. As a result, it is possible to measure IMT with high accuracy by calculating the distance between the detected boundaries.

In this case when a plurality of local maximal points appear in the lumen side in the brightness distribution due to the factors such as noise, it is preferable that the local maximal point having the maximum brightness gradient as well as being close to the lumen side is set as the tunica intima reference point. With such setting, the tunica intima reference point can be set properly in the tunica intima. Here the local maximal point close to the lumen side means that it is the local maximal point, when the local maximal point having the maximum brightness is set as the tunica externa reference point, positioned more on the lumen side than the tunica externa reference point.

As for the region-extracting method in such IMT measurement, the region growing method can be used. The region growing method is a method to set the reference point in the region to be extracted, and to extract the pixels wherein the brightness difference from the brightness of the reference point belong to the setting range. Therefore upon measurement of IMT, out of the local maximal points appearing in the brightness distribution in the thickness direction of the blood vessel wall in image data, the local maximal point on the lumen side is set as the tunica intima reference point and the local maximal point having the maximum brightness is set as the tunica externa reference point. And by extracting the pixels wherein the brightness difference from the brightness of the respective reference points belong to the setting range, the region formed by the pixels corresponding to the tunica intima or the region formed by the pixels corresponding to the tunica externa can be extracted.

Also, the setting range of the brightness upon extracting the pixel region can be set as the range from the brightness of the tunica intima reference point to the average brightness in the setting region equivalent of the lumen, or the range from the brightness of the externa reference point to the average brightness in the setting region equivalent of the range between the tunica externa reference point and the tunica intima reference point. In this way IMT can be measured with high accuracy regardless of the individual variability of the object since the brightness range is set with respect to each object.

Furthermore, signal processing means with a filter for highlighting the contour of the pixel region being extracted by the extraction means can be comprised. By comprising such means the contour of the extracted region is emphasized, thus for example, the boundary between the lumen and the tunica intima (the inner wall of the tunica intima) is clarified which makes it easier to extract the inner wall of the tunica intima. Therefore IMT can be measured accurately even when the boundary of the extracted region is unclear due to factors such as noise.

Also, there are occasions that the local maximal point does not appear in the lumen side of the brightness distribution due to factors such as noise. Given this factor, the ultrasound apparatus of the present invention comprises:

imaging means for obtaining image data regarding blood vessels by ultrasonic images;

Doppler imaging means for obtaining color Doppler image data of blood vessels;

brightness distribution acquisition means for acquiring the brightness distribution in the thickness direction of a blood vessel wall in image data;

color information acquisition means for acquiring color information of the respective pixels in the thickness direction of the blood vessel wall in color Doppler image data;

setting means for setting the local maximal point, out of the local maximal points appearing in the brightness distribution, having the maximum brightness as the tunica externa reference point;

extraction means for extracting, with respect to the respective pixels of the setting region, the pixels wherein the brightness belongs to the setting range including the tunica externa reference point; and calculation means for calculating the distance between the boundary of the lumen and the tunica intima of the blood vessel being obtained based on the color information and the boundary on the tunica intima side in the region being formed by the pixels extracted based on the tunica externa reference point.

It means that in color Doppler images, the pixels equivalent of the lumen where blood flows is displayed in color, and the pixels equivalent of the lumen where there is no blood flow is displayed in black and white. Therefore, the pixel coordinate equivalent of the boundary of the lumen and the tunica intima can be detected by determining the color information of the color Doppler image with respect to each pixel. As a result, the boundary of the lumen and the tunica intima (the inner wall of the tunica intima) can be detected even when the local maximal point on the lumen side of the brightness distribution does not appear due to the factors such as noise.

BRIEF DESCRIPTION OF THE DRAWINGS

FIG. 4 is a diagram for representing the process of FIG. 8 on the display screen, and the display example indicating the processing result of FIG. 3.

FIG. 6 is a diagram representing the process of FIG. 5 on the display screen, and the display example showing the processing result of FIG. 5.

BEST MODE FOR CARRYING OUT THE INVENTION

The First Embodiment

Figure 1:
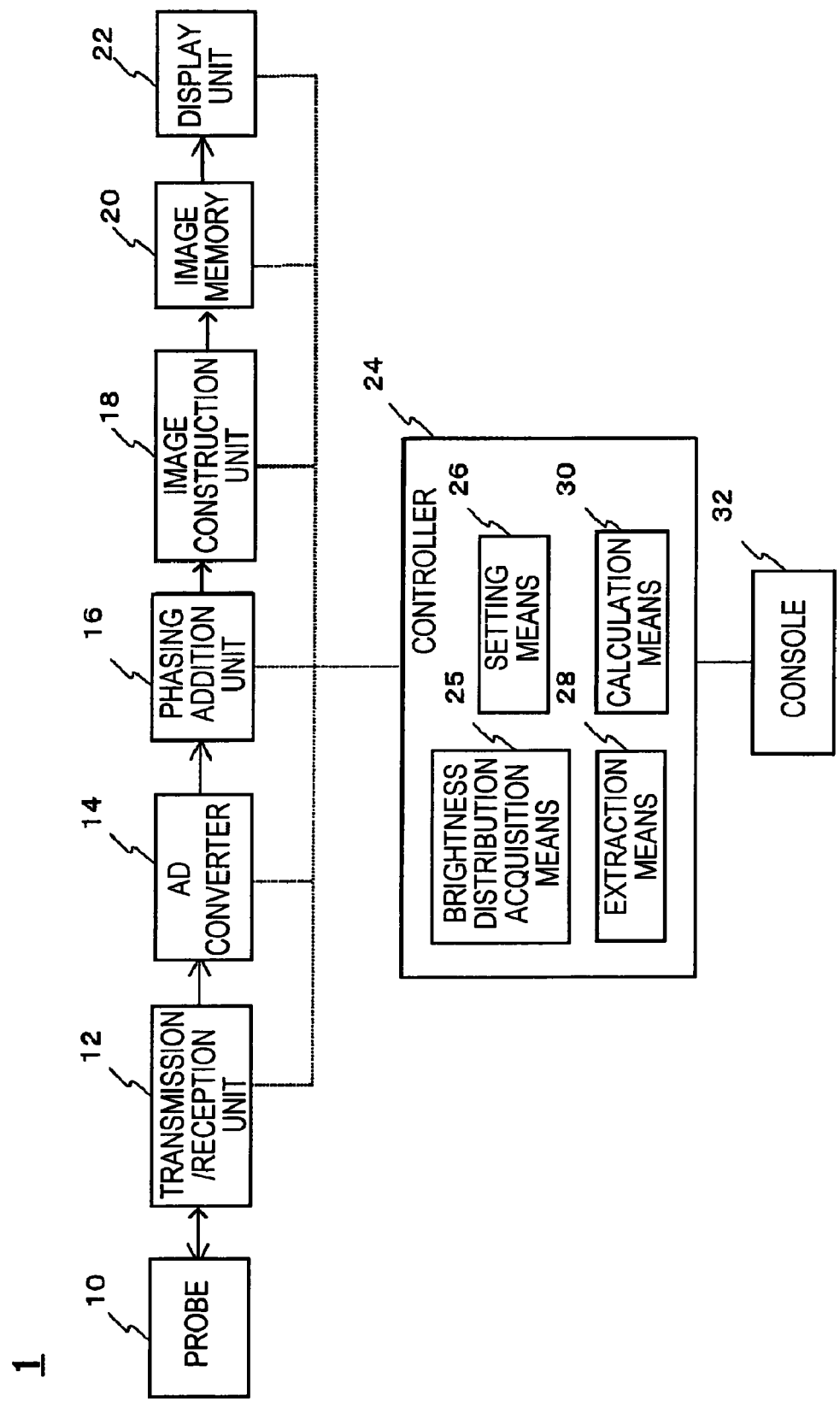
FIG. 1 is a block diagram of the ultrasound apparatus in the present embodiment to which the present invention is applied.

The first embodiment of the ultrasound diagnostic apparatus to which the present invention is applied as a medical imaging diagnostic apparatus will now be described referring to FIG. 1~FIG. 6. The present embodiment is an example of measuring IMT (composite thickness of the tunica intima and the tunica media) by applying the region growing method as a region extracting method corresponding to ultrasound images. FIG. 1 is a block diagram of the ultrasound diagnostic apparatus in the present embodiment.

As shown in FIG. 1, the ultrasound diagnostic apparatus is provided with imaging means for imaging the ultrasonic image with regard to an object (for example, a blood vessel). Imaging means comprises units such as:

probe 10 for transmitting/receiving ultrasonic waves between the object;

transmission/reception unit 12 for providing drive signals to probe 10 as well as receiving the transmission of reflected echo signals outputted from probe 10;

analog digital converter 14 (hereinafter referred to as AD converter 14) for converting the reflected echo signals outputted from transmission/reception unit 12 into digital signals;

phasing addition unit 16 for performing phasing addition on the reflected echo signals outputted from AD converter 14;

image construction unit 18 for reconstructing ultrasonic images (for example, tomograms) based on the reflected echo signals outputted from phasing addition unit 16;

storage means 20 for storing the ultrasonic images reconstructed by image construction unit 18 as image data (hereinafter referred to as image memory 20); and display unit 22 for displaying the ultrasonic images read out from image memory 20. Also, controller 24 is provided for outputting the commands to the units such as transmission/reception unit 12, AD converter 14, phase addition unit 16, image construction unit 18, image memory 20, and display unit 22.

Controller 24 has a function for measuring the composite thickness of the tunica intima and tunica media (IMT) of a blood vessel. For example, as shown in FIG. 1, controller 24 comprises brightness distribution acquisition means 25, setting means 26, extraction means 28 and calculation means 30. Brightness distribution acquisition means 25 is for acquiring the brightness distribution in the thickness direction of a blood vessel wall in a tomogram with regard to the blood vessel read out from image memory 20. Setting means 26 is for setting the local maximal point, out of the local maximal points appearing in the brightness distribution, on the lumen side as the tunica intima reference point, as well as setting the local maximal point having the maximum brightness as the tunica externa reference point. Extraction means 28 is for extracting the pixels, with respect to the each pixel in the setting range including the tunica intima reference point or the tunica externa reference point, wherein the brightness belong to the setting range. Calculation means 30 is for calculating the distance between the boundary in the blood vessel wall side in the region formed by the pixels being extracted based on the tunica intima reference point (the inner wall of the tunica intima) and the boundary in the lumen side in the region formed by the pixels being extracted based on the tunica externa reference point (the inner wall of the tunica externa). In addition, brightness distribution acquisition means 25, setting means 26, extraction means 28 and calculation means 30 are implemented by programs containing the description of commands, and are written in, for example, DSP (Digital Signal Processor) of controller 24. Also, console 32 is connected to controller 24. The input parameters are transmitted to controller 24 via console 32.

The basic operation of the ultrasound diagnostic apparatus 1 with such configuration will now be described. First probe 10 is brought into contact with the body surface of an object being examined. Next, drive signals are provided from transmission/reception unit 12 to probe 10 in answer to the command of controller 24. Through this operation ultrasonic waves are transmitted from probe 10 to, for example, the carotid artery. The ultrasonic waves reflected by the carotid artery are received by probe 10 as reflected echo signals. The process such as amplification is implemented on the received reflected echo signals by transmission/reception unit 12. The reflected echo signals being outputted from transmission/reception unit 12 are first converted into digital signals by AD converter 14, and phasing addition process is carried out on the converted digital signals by phasing addition unit 16. The reflected echo signals outputted from phasing addition unit 16 are reconstructed by image construction unit 18 through implementing a process such as demodulation. The reconstructed tomogram is stored in image memory 20 as image data. The stored ultrasonic images are displayed on display unit 22 by being read out according to the command of controller 24.

With such ultrasound diagnostic apparatus, IMT of blood vessel walls is measured in order to identify diseases such as arteriosclerosis or cardiovascular disorder. A blood vessel wall, as will be described later, is formed with a triaminar structure consisting of tunica intima, tunica media and tunica externa in due order from the lumen side where blood flows. IMT is the sum of the thickness of tunica intima and the thickness of tunica media, in other words the distance from the inner wall of tunica intima to the inner wall of tunica media. In the present embodiment, the inner wall of the tunica intima and the inner wall of the tunica externa will be detected with precision, and the measurement accuracy of IMT will be improved by applying the region growing method as the region extracting method with respect to the tomogram of blood vessels.

The region growing method will now be described. Extraction means 28 sets a point in the set region of interest as reference points (x,y), and then sets the threshold or its width to make the width of the pixels in the region noted. For example, the width "m" is set in regard to the pixel value "n" of the reference point displayed on display unit 22 (n,m are discretional integers). Therefore, the threshold width is given as "n±m", the lower limit threshold as "n−m" and the upper limit threshold as "n+m". Controller 24 detects the pixels that are surrounding the reference point, and connects the regions that have the pixel value within the threshold range. Eventually the region that includes the reference point and has the pixel value within the threshold range is obtained. This region will be displayed on display unit 22.

Figure 2:
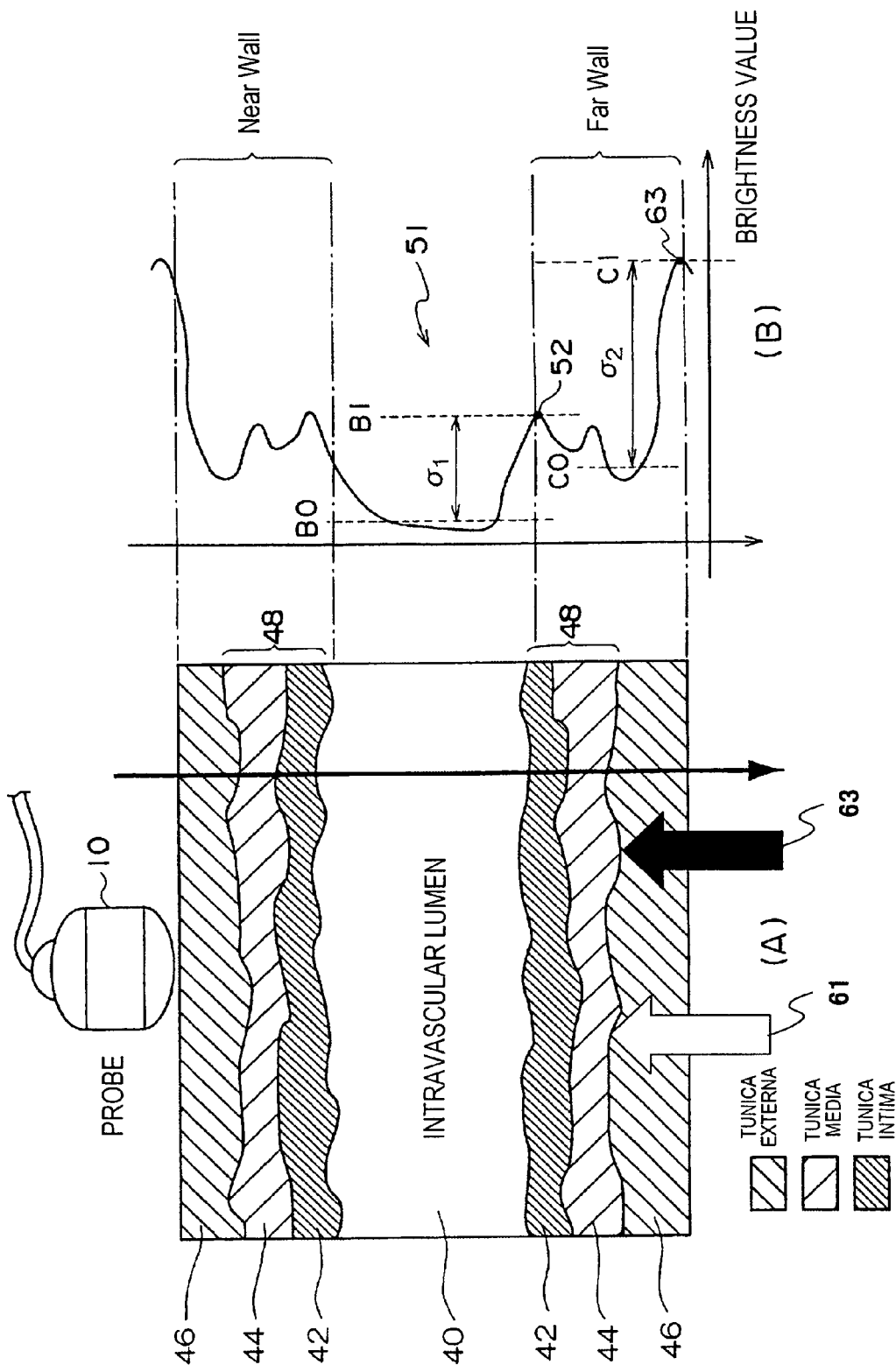
FIG. 2 is an ultrasound image showing the cross-sectional view of a blood vessel wall of carotid artery in the thickness direction, and the brightness distribution line of a blood vessel wall in the thickness direction.

The process for IMT measurement in the present invention will be described referring to FIG. 2~FIG. 6. FIG. 2 (A) is a tomogram showing the cross-sectional view of a blood vessel wall of a carotid artery in the thickness direction. FIG. 2 (B) is the brightness distribution of FIG. 2 (A) in the thickness direction of the blood vessel wall, with the vertical axis indicating the depth and the horizontal axis indicating the brightness value.

As shown in FIG. 2(A), the carotid artery is formed by the blood vessel wall circularly surrounding lumen 40 where blood flows. A blood vessel wall is formed with a triaminar structure consisting of tunica intima 42, tunica media 44 and tunica externa 46 of a blood vessel in due order from the side of lumen 40. Here, the sum of the thickness of tunica intima 42 and the tunica media 44 are referred to as IMT 48. In other words, IMT 48 is defined as the sum of the thickness of tunica intima 42 and tunica media 44 on the straight line that is vertical to the inner wall of tunica externa 46 in the blood vessel. Also for the convenience of explanation, the blood vessel wall which is close to the side of probe 10 being contacted to the body surface of the object is referred to as the near wall, and the blood vessel on the side which is far from probe 10 is referred to as the far wall.

Figure 3:
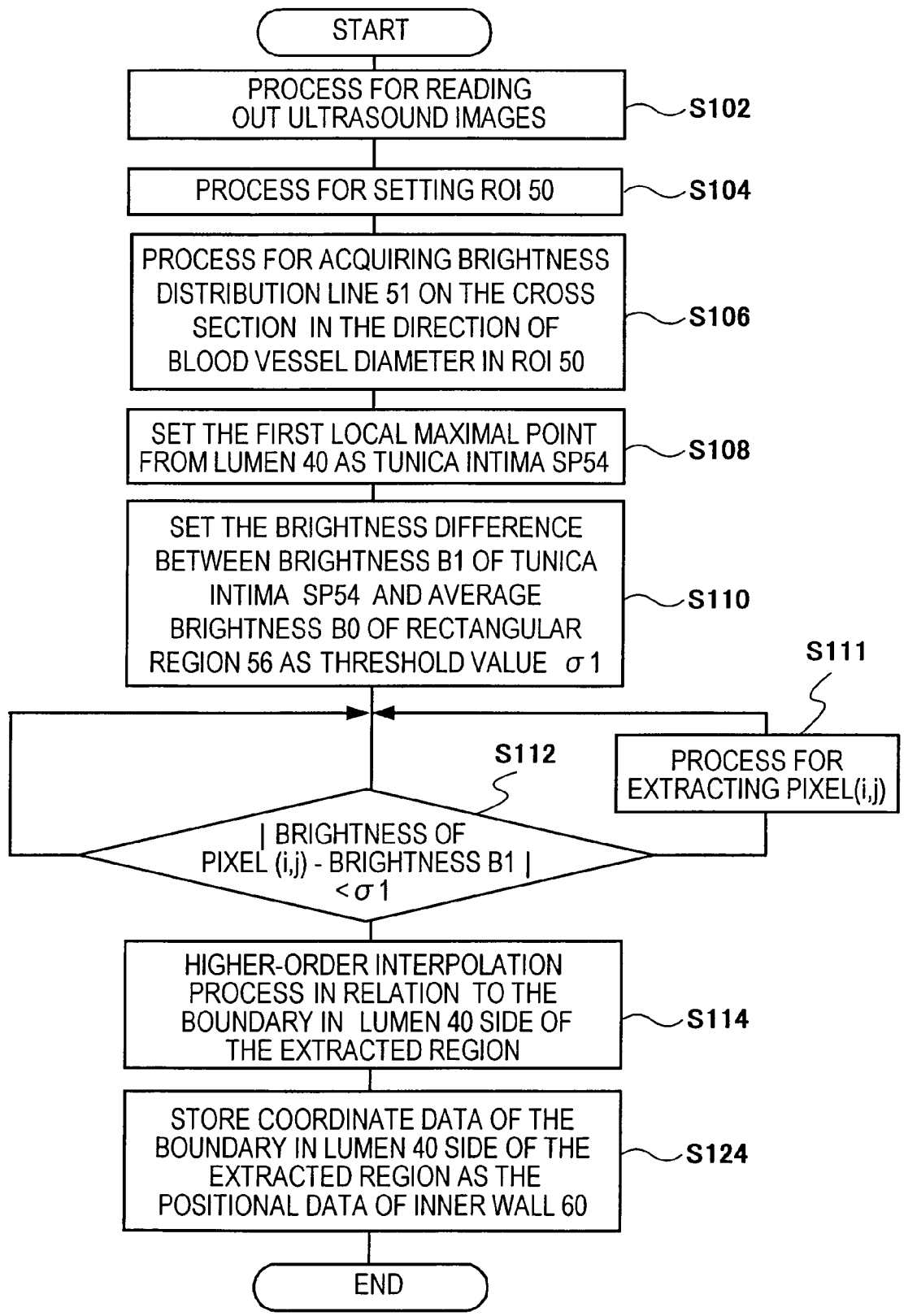
FIG. 3 is a flow chart indicating the process for obtaining the inner wall of the tunica intima.

FIG. 3~FIG. 6 is a diagram for describing the IMT measurement of the far wall. FIG. 3 is a flow chart showing the process for obtaining the inner wall of tunica intima 42, the upper level of FIG. 4 is a diagram for showing the process of FIG. 3 on a display screen, and the lower level is the display example showing the processing result of FIG. 3. The case of measuring IMT of the near wall will be basically the same.

As shown in FIG. 3~FIG. 4, the tomogram stored in image memory 22 is read out by brightness distribution acquisition means 25 according to command of controller 24 (S102). A tomogram shows a radial cross-sectional view of the blood vessel. The read out tomogram will be displayed on display unit 22.

Region of interest 50 (hereinafter referred to as ROI50) is set to the read out tomogram (S104). ROI50 is a determinate region being set from the far wall to lumen 40 via a device such as a mouse on console 32 on the tomogram being displayed on display unit 22. A discretional position within ROI50 is assigned or automatically determined via console 32. Brightness distribution line 51 in the thickness direction of the far wall in the determined position is obtained by brightness distribution acquisition means 25 (S106, FIG. 2(B)). Out of the local maximal points appearing in the obtained brightness distribution line 51, the position equivalent of local maximal point 52 on the side of lumen 40 is set as lumen reference point 54 (hereinafter referred to as tunica intima SP (Source Point) 54)) by setting means 26 (S108). Here, for example, when a plurality of local maximal points appear on the side of lumen 40 in brightness distribution line 51 due to factors such as noise, a point close to lumen 40 and has the maximum brightness gradient can be set as tunica intima SP54. The local maximal point close to lumen 40 means that when local maximal point 63 having the maximum brightness is set as tunica externa reference point 64, it is local maximal point 52 positioned on the side of lumen 40 closer than tunica externa reference point 64 and a point equivalent of tunica intima 42.

Next, threshold value σ1 for extracting the pixels corresponding to tunica intima 42 using the region growing method is set by extraction means 28 (S110). For example, rectangular region 56 which is 5 pixel away from tunica intima SP54 to the side of lumen 40 while having the width of 3 pixels in the blood flow direction from tunica intima SP54 and 3 pixels in the opposite direction of blood flow is set. The shape of the region may be other than a rectangle. The point is to set the region in the position equivalent of lumen 40. Next, average brightness B0 of the pixels in rectangular region 56 is obtained. The absolute value of the brightness difference between the obtained average brightness B0 and brightness B1 of tunica intima SP54 is set as threshold value σ1. Also, other means such as weighted average may be used in place of average brightness B0.

Based on threshold value σ1, the region formed by the pixels equivalent of tunica intima 42 is extracted by extraction means 28. In the present embodiment, the region growing method is applied as a region extracting method. For example, with respect to the pixels adjoining tunica intima SP54, the absolute value of the brightness difference between brightness B2 of the pixel thereof and brightness B1 of tunica intima SP54 are obtained. The obtained value and threshold value σ1 are compared (S111). The pixels having brightness B2 are extracted due to the assessment that the pixel having brightness B2 is equivalent of tunica intima 42 when the absolute value of the brightness difference is smaller than threshold value σ1 (S112). If the brightness difference is bigger than threshold value σ1, the pixel does not get extracted. Basically, the pixels that belong to the setting range from average brightness 50 to brightness B1 of tunica intima SP 54 are extracted by setting threshold value σ1 as the reference. Such process is sequentially carried out on each pixel (i, j) of ROI50 including tunica intima SP54. Here, "i" is the pixel value of a horizontal axis in the ultrasound image and "j" is the pixel value of a vertical axis. Also, the region for implementing extraction means may be set as the region of the entire ultrasound image, or it can be limited to the additionally set specified region.

Through the process of S111 and S112, the pixels corresponding to tunica intima SP42 are extracted by extraction means 28. In consequence, as shown in the lower level of FIG. 4, extracted region 58 is formed by the extracted pixels. The boundary on the side of lumen 40 of extracted region 58 corresponds to inner wall 60 of tunica intima 42. The pixels corresponding to extracted region 58 or inner wall 60 may be displayed in color.

The boundary corresponding to inner wall 60 is obtained in pixel unit. Therefore in regard to the coordinate data of the boundary corresponding to inner wall 60, an interpolation process such as least squares method or approximation is implemented by calculation means 30. The interpolated coordinate data is stored as the positional data of inner wall 60 of tunica intima 42 (S116). As the storage region of the positional data, the buffer region comprised in controller 24 is used.

Figure 5:
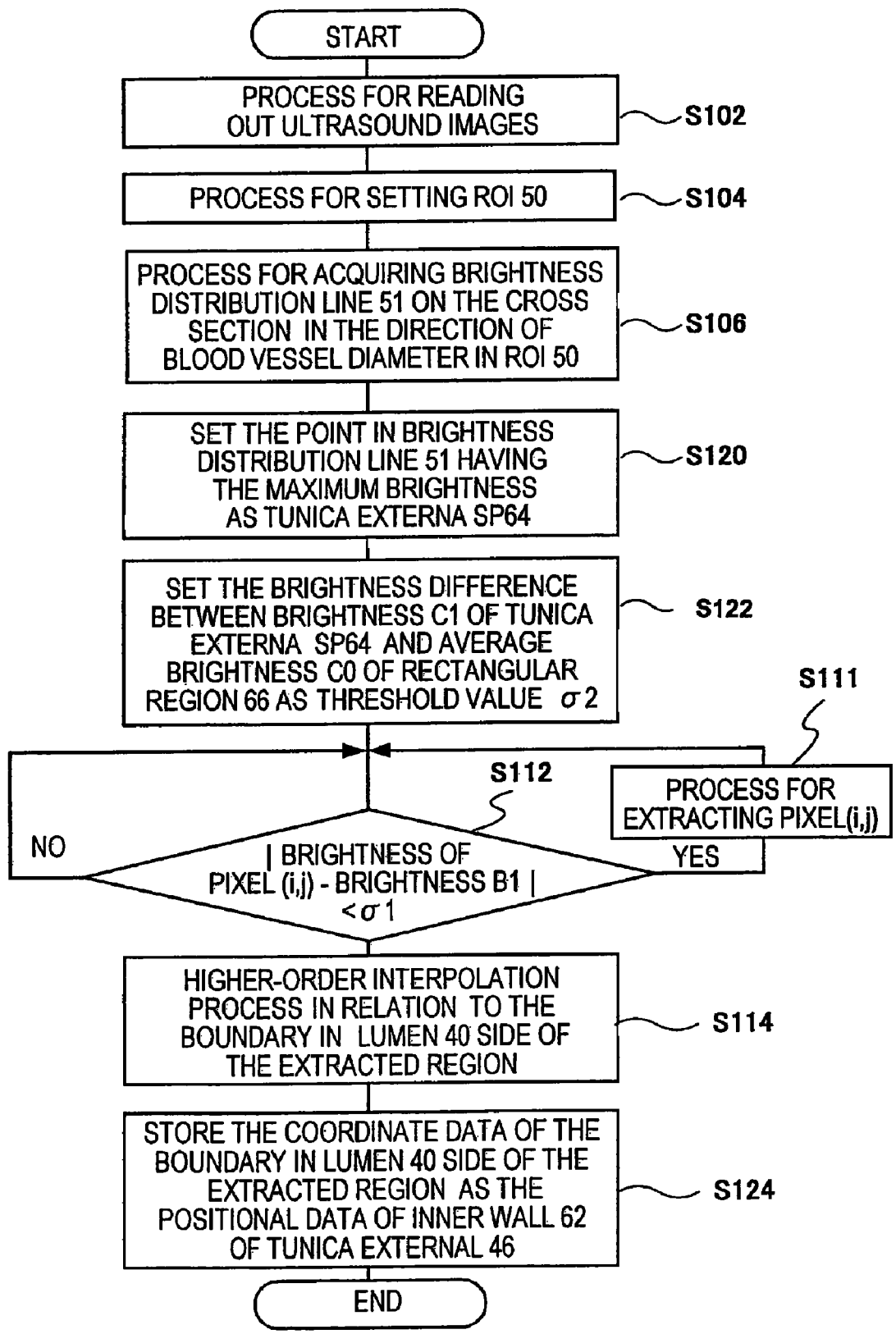
FIG. 5 is a flow chart showing the process for obtaining the inner wall of the tunica externa.

FIG. 5 is a flow chart showing the process for obtaining the inner wall of tunica externa 46, the upper level of FIG. 6 is a diagram illustrating the process of FIG. 5 on the display screen, and the lower level is a display example showing the processing result of FIG. 5. The process illustrated in FIG. 5 is the same as the process illustrated in FIG. 3 in the point of extracting the pixels wherein the brightness belong to the setting range by the region growing method, but different in the setting of the reference point or the threshold value. For example, with regard to brightness distribution line 51 in the thickness direction of the far wall, the coordinate of point 63 having the maximum brightness is set as tunica externa reference point 64 (hereinafter referred to as tunica estima SP (Source Point) 64) (S120, FIG. 2(B)).

Next, threshold value σ2 for obtaining the boundary between tunica externa 46 and tunica media 44 is set by extraction means 28 (S122). For example as shown in FIG. 6, rectangular region 66 which is positioned between tunica externa SP64 and tunica intima SP54 while having the width of 3 pixels in the blood flow direction from tunica externa SP64 and 3 pixels in the opposite direction of blood flow is set. Since the brightness of the pixels corresponding to tunica intima 42 and the pixels corresponding to tunica media 44 are almost the same in a tomogram, rectangular region 66 (for example, the region including tunica intima SP54) may be set in the position equivalent of tunica intima 42. The point is to set the region from tunica externa 46 to tunica media 44 (or tunica intima 42).

Next, average brightness C0 of the pixels in rectangular region 66 is obtained by extraction means 28. The brightness difference between the obtained average brightness C0 and brightness C1 of tunica externa SP64 is set as threshold value σ2. Then the extracting process of the pixels is carried out in relation to pixel (i,j) of ROI50 including tunica externa SP64 in the same manner as the process shown in FIG. 3. For example, the pixels of the extracting target is extracted when the brightness difference between the brightness of the pixels of extracting target and brightness C1 of tunica externa SP64 belong to the setting range. Here, the setting range is the range from average brightness 68 to brightness C1 of tunica externa SP64. Extracted region 68 formed by the extracted pixels is equivalent of tunica externa 46. Therefore after carrying out the interpolation process on the coordinate data of the boundary on the side of lumen 40 in extracted region 68, the coordinate data thereof is stored as the positional data of the inner wall 62 of tunica estima 46 (S124).

Based on the positional data being obtained by such process shown in FIG. 3~FIG. 6, IMT is calculated by calculation means 30. For example, based on the positional data of inner wall 60 of tunica intima 42 being stored in S116 of FIG. 3 and the positional data of inner wall 62 of tunica externa 46 being stored in S124 of FIG. 5, the distance between inner wall 60 of tunica intima 42 and inner wall 62 of tunica externa 46 is obtained by calculation means 30. IMT 48 is defined as the sum of the thickness of tunica intima 42 and the thickness of tunica media 44 on the straight line that is vertical to the inner wall of the tunica estima in the blood vessel, which is the distance from inner wall 60 of tunica intima 42 to inner wall 62 of tunica externa 46. Also, besides measuring IMT of predetermined position of a blood vessel, other values such as the percentage rate of IMT may be measured. The calculation result of IMT will be displayed on display unit 22.

Since the acoustic impedance of the lumen 40 is comparatively greater than the acoustic impedance of the tunica intima of a blood vessel in general, the brightness difference between the pixels of lumen 40 and the pixels of tunica intima 42 in an ultrasound image turns out to be great. Also, since the acoustic impedance of the tunica externa 46 is comparatively greater than the acoustic impedance of the tunica media 44 of a blood vessel in general, the brightness difference between the pixels of tunica media 44 and the pixels of tunica externa 46 in an ultrasound image also turns out to be great. Therefore in the present embodiment, by properly setting the range of the brightness of pixels for being extracted, it is possible to extract the pixels corresponding to tunica intima 42 or tunica externa 46. As a result, it is possible to measure IMT with high accuracy since the positional data on inner wall 60 of tunica intima 42 or inner wall 62 of tunica externa 46 can be detected precisely from the coordinate data of extracted region 58 or extracted region 68.

Also in the present embodiment, the brightness difference between brightness B1 of tunica intima SP54 and average brightness B0 of rectangular region 56 which is equivalent of lumen 40 is set as threshold value σ1. As threshold value σ2, the brightness difference between brightness C1 of tunica externa SP64 and average brightness C0 of rectangular region 66 which is equivalent of tunica media 44 is set. In other words, threshold value σ1 and threshold value σ2 are set from a tomogram relating to a blood vessel with respect to each object. Therefore it facilitates the accurate IMT measurement regardless of individual variability of objects being examined.

Moreover in place of setting rectangular regions 56 or 66 on a tomogram, they can be set on automatically in the position determined in advance in relation to ROI50. This automatic setting of threshold value σ1 or threshold value σ2 improves usability of the apparatus.

Also, the identification of the near wall and the far wall can be determined automatically by brightness distribution line 51 within the setting region. For example, the above-mentioned IMT measurement can be carried out by first defining with respect to each of the setting region bisected horizontally that the one with smaller summation of the brightness value is on the lumen side of the blood vessel, then automatically determining that if the lumen is on the lower side of the setting range it is the near wall and if it is on the upper side it is the far wall. Although IMT measurement was performed on either near wall or far wall, IMT measurement of the two walls may be combined. In concrete terms, IMT measurement is performed individually on the near wall and far wall, and the IMT measurement value of the near wall and far wall are compared with each other. Then the greater measurement value of the two is determined as the IMT measurement value of the relevant cross section. Or, the average value of IMT measurement value of the near wall and far wall may be determined as the IMT measurement value of the relevant cross section. Since IMT measurement value varies according to the axis direction, by using the two IMT measurement values of the near wall and far wall the accuracy is improved.

IMT measurement is performed based on inner wall 60 of tunica intima 42 and inner wall 62 of tunica externa 62 being extracted by an region extracting method. Usual IMT measurement is performed on 1 line in a direction vertical to the blood vessel axis direction. In the present embodiment, within the region wherein inner wall 60 of tunica intima 42 and inner wall 62 of tunica externa are extracted, calculation means 30 carries out the calculation of the average value, maximum value or minimum value of IMT, and the resulting value of the calculation is displayed on display means 22. As for the maximum value and the minimum value, the location of the maximum value and the location of the minimum value in the extracted region are marked on display unit 22. For example, as shown in FIG. 2, the minimum value is displayed with white arrow 61 and maximum value with black arrow 63.

Such measurement of IMT maximum value enables the diagnosis of pernicious regions in extracted regions. Also, the influence of noise signals can be minimized by measuring the average value of IMT even when noise signals appear on an image of a part of extracted regions.

Also, the setting of tunica intima reference point 80 and tunica externa reference point 64 may be implemented arbitrarily by console 32. While the measurement is performed on an ultrasound apparatus in the above description, IMT measurement can also be implemented on medical imaging diagnostic apparatuses such as CT, MR or X-ray apparatus in the same manner using the region extracting method.

The second embodiment of the ultrasound apparatus to which the present invention is applied as a medical imaging diagnostic apparatus will now be described. The difference of the present embodiment from the first embodiment is that the threshold is made variable. Thus the description of the present embodiment will focus on differences from the first embodiment. Places that are mutually corresponding will be described with the same encoding.

As described in the first embodiment, for example, the brightness difference between average brightness B0 of rectangular region 56 and brightness B1 of tunica intima SP54 is set as threshold value σ1. However, there are occasions that errors are included in average brightness B0 due to factors such as noise generated in the pixels of rectangular region 56.

From this perspective, in this embodiment the credibility of extracted region 42 is increased by changing the threshold value σ1 in incremental steps via console 32. This will also be the same for the case in threshold value σ2. For example, GUI (Graphical User Interface) for changing threshold value σ1 is displayed on display unit 22. Threshold value σ1 is interactively increased via GUI in incremental steps. Each time threshold value σ1 increases, the process of S111 and S112 in FIG. 3 will be carried out. By proceeding these steps, the extracted regions (for example, extracted regions S1, S2, S3 . . . ) corresponding to the threshold of the respective steps can be obtained. The respective areas of the obtained extracted regions S1, S2, S3 . . . are calculated by calculation unit 30. The area changing rate of the respective steps are further obtained. The obtained changing rate makes relatively drastic change. In other words, in the process of changing threshold value σ1 in incremental steps, there are steps where the area of the extracted region increases drastically due to the pixels corresponding not only to tunica intima 42 but also to lumen 40. Therefore, the extracted region in the step before the area increases rapidly is identified as equivalent only to tunica intima 42. In place of the changing rate of the area, the area difference may also be obtained. This is also the same for tunica externa 46.

According to the present embodiment, an extracted region (also a threshold) can be detected when the area of the extracted region increases drastically as changing threshold value σ1 in incremental steps (or gradually). Therefore, even when errors are included in average brightness B0 the accuracy of extracted regions will be increased. Moreover, the accuracy of IMT measurement will be improved by fine adjusting the detected threshold.

The Third Embodiment

The third embodiment of the ultrasound apparatus to which the present invention is applied as a medial imaging diagnostic apparatus will now be described referring to FIG. 7. The difference of the present embodiment from the first embodiment is to decrease the error of setting tunica intima SP54 by mistake. Thus the description of the present embodiment will focus on differences from the first embodiment. Places that are mutually corresponding will be described with the same encoding.

In brightness distribution line 51 of FIG. 2, there are occasions that tunica intima SP54 instead of tunica intima 42 is set by mistake when, for example, a plurality of local maximal points appear on the side of lumen 40 due to factors such as noise. Given this factor, in the present embodiment, a plurality of brightness distribution lines in the vessel diameter direction (depth direction) is obtained over the blood flow direction (lateral direction), and tunica intima SP54 is set based on the average brightness distribution line of the obtained respective brightness distribution lines.

Figure 7:
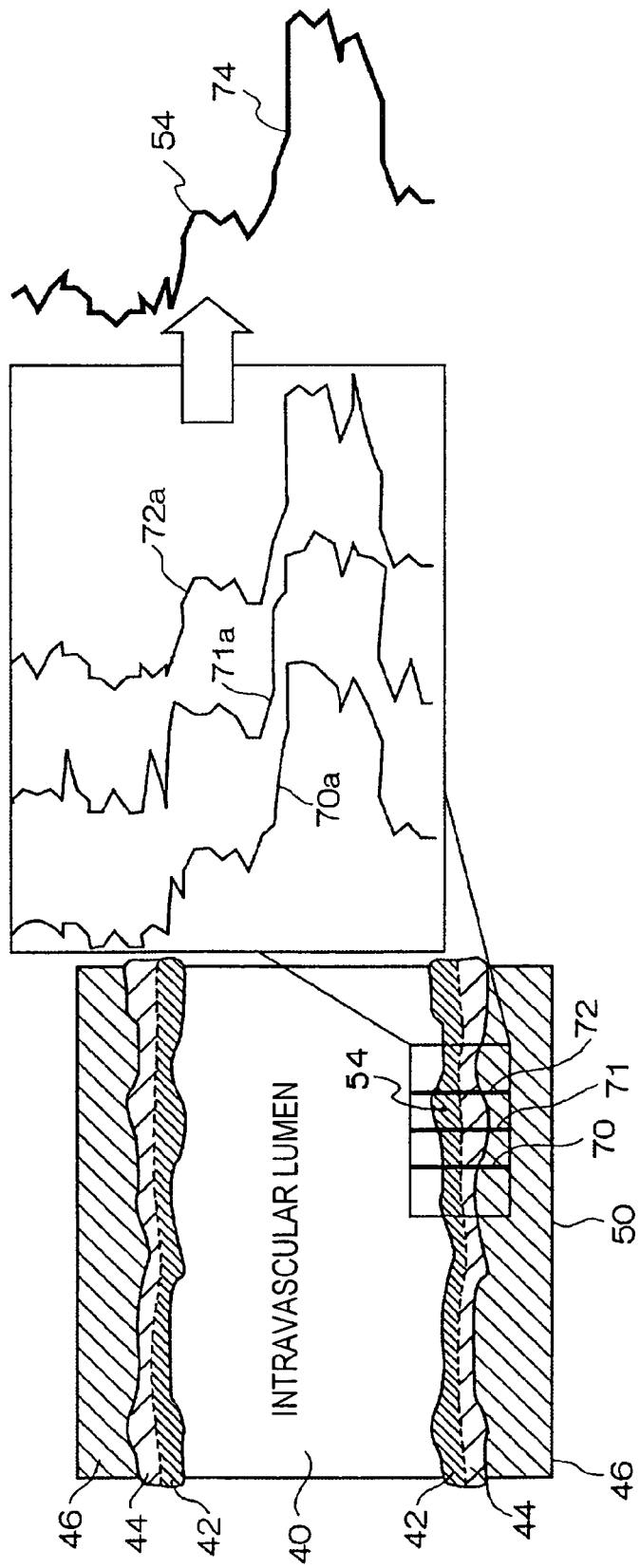
FIG. 7 is an explanatory diagram of the setting method of the tunica intima reference point in the third embodiment of the present invention.

For example, 3 arbitrary directions 70, 71 and 72 being parallel to the vessel diameter direction within ROI50 are set as shown in FIG. 7. Brightness distribution lines 70a, 71a and 72a of set respective directions 70, 71 and 72 are obtained by brightness distribution acquisition means 25. Average brightness distribution line 74 of respective brightness distribution lines 70a, 71a and 72a is obtained. Out of the local maximal points appearing on the obtained average brightness distribution line 74, the first local maximal point which is closest to lumen 40 and has the maximum brightness gradient is set as tunica intima SP54.

According to the present embodiment, even when one brightness distribution line 70a is influenced by noise, tunica intima SP54 is set by average brightness distribution line 74 based on three brightness distribution lines. This decreases the influence of noise in the setting of tunica intima SP54, which also means that the possible error of setting tunica intima SP54 other than tunica intima 42 by mistake is also decreased.

Although the example of obtaining the brightness distribution in 3 directions has been described, the number of the brightness distribution lines for acquisition is not limited, and the possibility of making errors in setting can be further decreased as the number of lines is increased. While the example of obtaining the average brightness was described, other statistical applications exist. The point is to be able to determine the gradient of the brightness information with addition of several points in lateral direction. The present embodiment can also be applied to tunica externa SP64.

The Fourth Embodiment

The fourth embodiment of the ultrasound apparatus to which the present invention is applied as a medical imaging diagnostic apparatus will now be described referring to FIG. 8. The difference of the present embodiment from the first embodiment is that the tunica intima SP54 is modified when it is set by error. Therefore, the description of the present embodiment will focus on differences from the first embodiment. Places that are mutually corresponding will be described with the same encoding.

Figure 8:
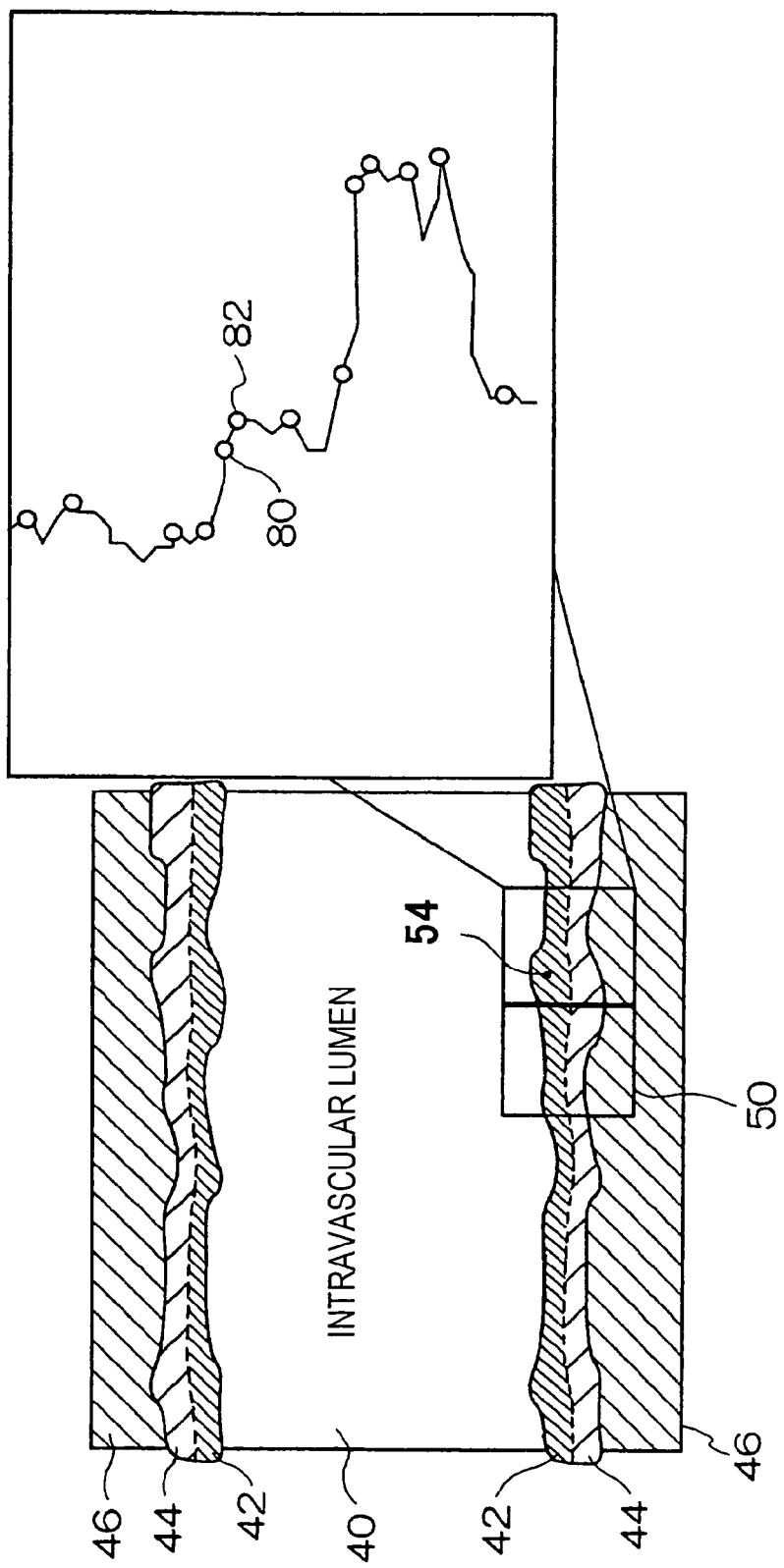
FIG. 8 is an explanatory diagram of the setting method of the tunica intima reference point in the fourth embodiment of the present invention.

As shown in FIG. 8, when a plurality of local maximal points 80 and 82 appear on the side of lumen 40 of the brightness distribution line, there are occasions that local maximal point 80 is set by error as tunica intima SP54. By implementing the region extracting method such as region growing method based on the set tunica intima SP54, the region corresponding to tunica intima 42 is extracted. The extracted region cuts across the pre-set range. In other words, the extracted region deviates from the expected result.

From this perspective, in the present embodiment, local maximal point 82 that is the next local maximal point on the side of tunica intima 42 from local maximal point 80 being set as tunica intima SP54 at the moment is reset as tunica intima SP54 either automatically or via, for example, console 32. The extracted region is obtained based on the reset tunica intima SP54. This process is repeated until the extracted region falls within the pre-set range.

The present embodiment enables the setting of tunica intima SP54 even more accurately. As for the resetting of tunica intima SP54, it can be carried out either before or after the region extraction. As an example of resetting before extracting the region, when local maximal point 80 is identified as obviously deviating from tunica intima 42, tunica intima SP54 can be modified by resetting local maximal point 80 to local maximal point 82 either automatically or via console 32. The modification of tunica externa SP64 can be carried out basically in the same manner.

The Fifth Embodiment

The fifth embodiment of the ultrasound apparatus to which the present invention is applied as a medical imaging diagnostic apparatus will now be described referring to FIGS. 9 and 10. The difference of the present embodiment from the first embodiment is that the contour of the extracted region is emphasized. Therefore, the description of the present embodiment will focus on differences from the first embodiment. Places that are mutually corresponding will be described with the same encoding.

Figure 9:
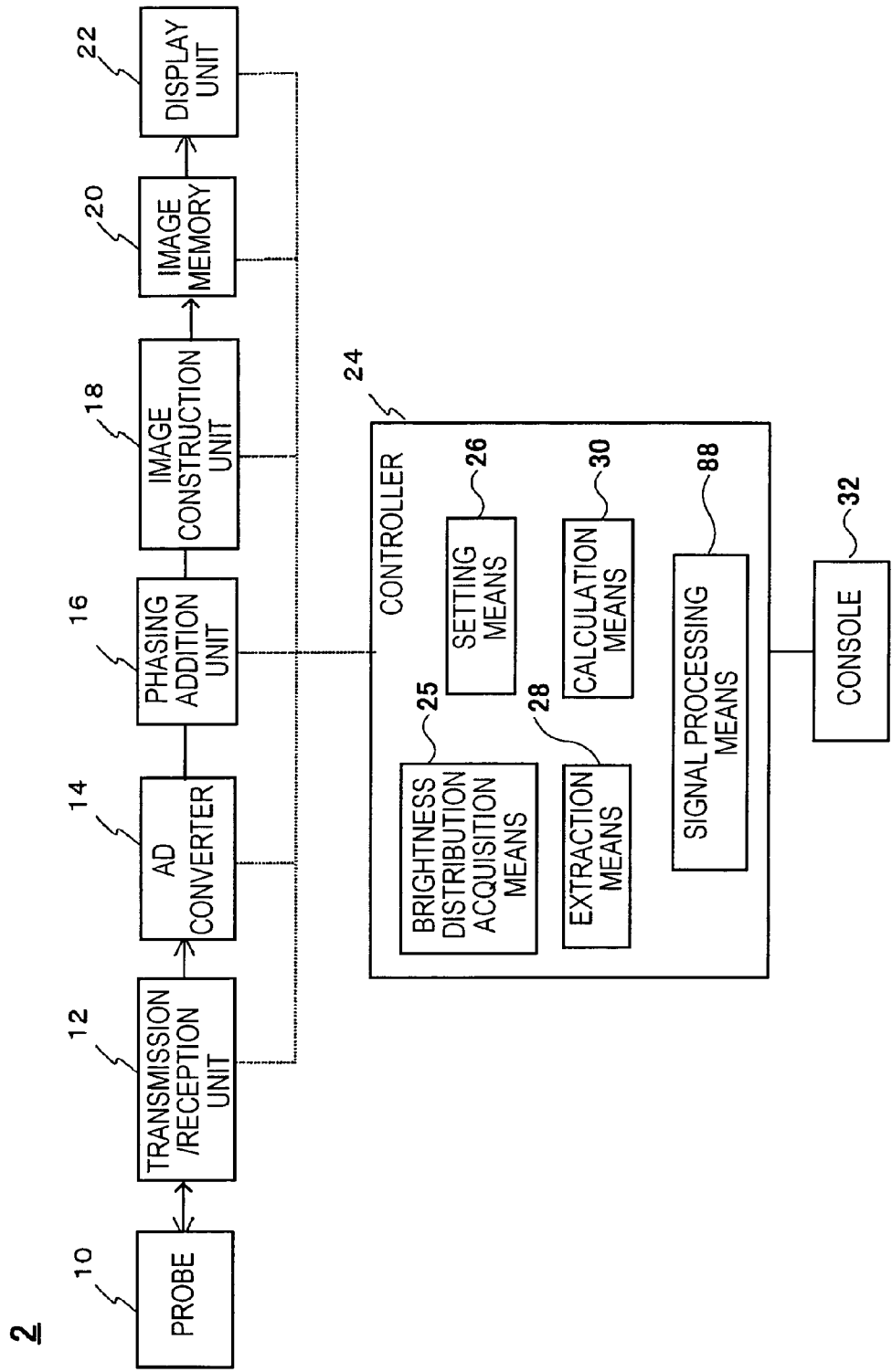
FIG. 9 is a block diagram of the ultrasound apparatus in the fifth embodiment of the present invention.

FIG. 9 is a block diagram of ultrasound diagnostic apparatus 2 in the present embodiment. As shown in FIG. 9, ultrasound diagnostic apparatus 2 has signal processing means 88 for emphasizing the contour of the extracted region being extracted by extraction means 28 mounted in controller 24. Signal processing means 88 is composed of a signal-processing filter such as an unsharp masking. Signal processing means 88 is software being installed in DSP (Digital Signal Processor) of controller 24. As for the signal-processing filter, any form that exerts an edge effect (sharpness effect) for emphasizing the contour of the extracted region on a tomogram can be used.

Figure 10:
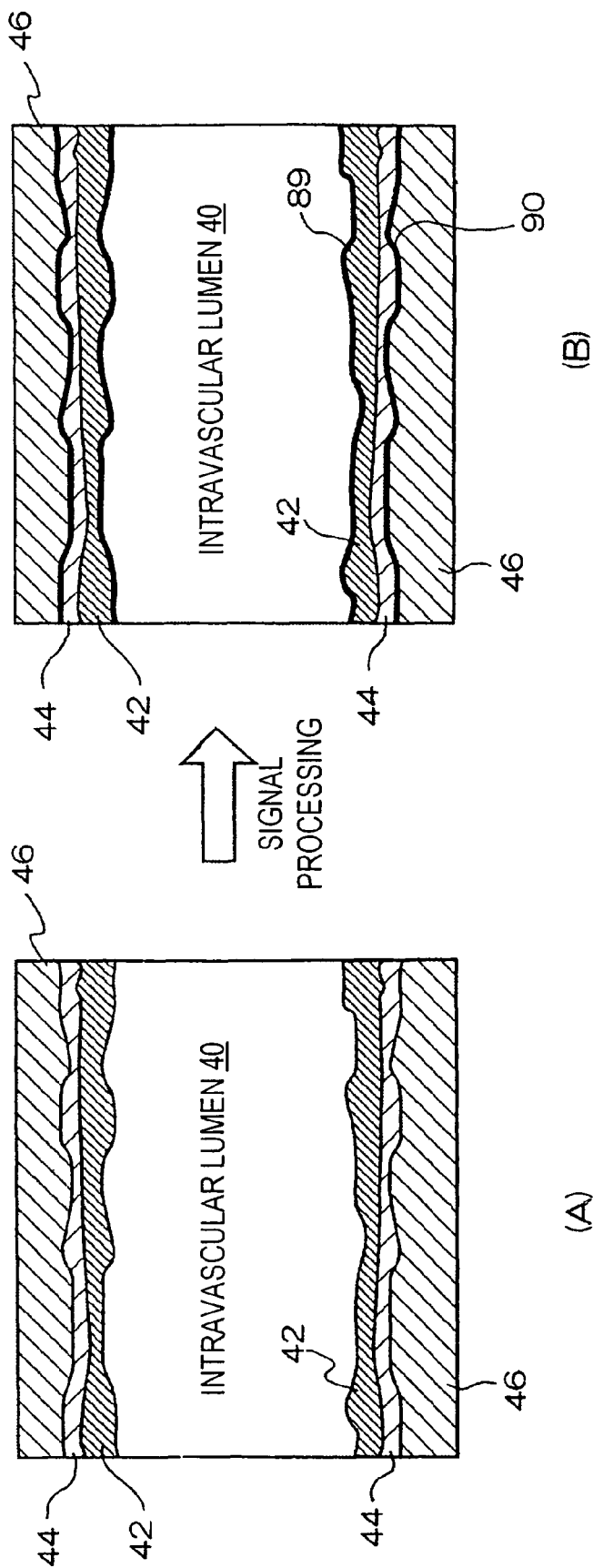
FIG. 10 is a display example of a tomogram for explaining signal processing means in FIG. 9.

FIG. 10 is a display example of the tomogram for illustrating the operation of signal processing means 88. FIG. 10(A) is a display example of an ultrasonic image of an extracted region (for example, the region corresponding to tunica intima 42). FIG. 10 (B) is a display example of an ultrasonic image implemented with the contour emphasizing process.

In FIG. 10 (A), there are occasions that the boundary between tunica intima 42 and lumen 40 of the blood vessel that is the inner wall of tunica intima 42 is blurred due to factors such as noise. In such cases it is difficult to detect the coordinate data of the inner wall of tunica intima 42 accurately which hinders the proper measurement of IMT.

In terms of this, in the present embodiment, the contour emphasizing process is carried out by signal processing means 88 in relation to the region extracted by extraction means 28. As a result, as shown in FIG. 10 (B), boundary 89 between tunica intima 42 and lumen 40 of a blood vessel that is the inner wall of tunica intima 42 is emphasized by signal processing means 88. Therefore, boundary 89 between tunica intima 42 and lumen 40 becomes distinct which decreases the false detection by error, and the coordinate data of boundary 89 between tunica intima 42 and lumen 40 can be obtained accurately.

In the same manner, the coordinate data of boundary 90 between tunica externa 46 and tunica media 44 that is the inner wall of tunica externa 46 can be accurately obtained. Thus IMT measurement can be accurately carried out from the respective coordinate data of the inner wall of tunica intima 42 and the inner wall of tunica externa 46. The command of signal processing means 88 to enable or disable the contour emphasizing function is inputted to controller 24 via console 32 according to the will of an operator. Also a plurality of filters with different contour emphasizing process can be installed in signal processing means 88. In this manner, the desired filter can be selected out of the plurality of filters according to the need.

The Sixth Embodiment

The sixth embodiment of the ultrasound diagnostic apparatus to which the present invention is applied as a medical imaging diagnostic apparatus will now be described referring to FIGS. 11~13. The difference of the present embodiment from the first embodiment is that the inner wall of tunica intima 42 is accurately obtained based on Doppler signals of the reflected echo signals generated from an object. Therefore, the description of the present embodiment will focus on differences from the first embodiment. Places that are mutually corresponding will be described with the same encoding.

Figure 11:
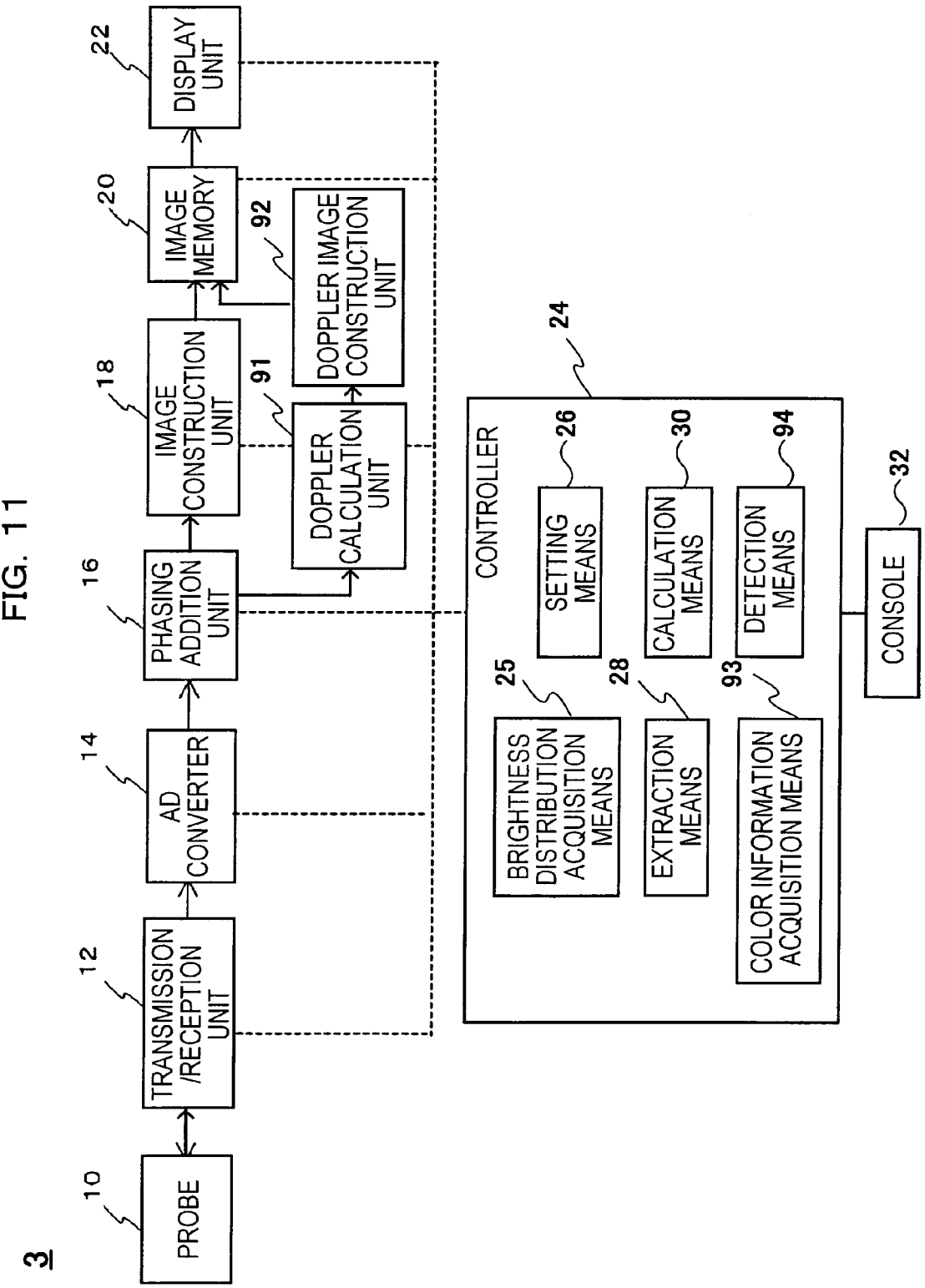
FIG. 11 is a block diagram of the ultrasound apparatus in the sixth embodiment of the present invention.

FIG. 11 is a block diagram of ultrasound diagnostic apparatus 3 of the present embodiment. As shown in FIG. 11, ultrasound apparatus 3 comprises Doppler imaging means for imaging color Doppler images with respect to an object being examined (for example, a blood vessel). Doppler imaging means comprises units such as Doppler calculation unit 91 and Doppler image construction unit 92. Doppler calculation unit 91 detects the phase difference of the reflected echo signals of the same region outputted from phasing addition unit 16 being shifted temporally, and the average frequency or the dispersion in relation to blood flow is obtained from the detected phase contrast. Doppler image construction unit 92 reconstructs color Doppler images by implementing color mapping according to the Doppler signals being obtained by Doppler calculation unit 91, and stores the reconstructed color Doppler signals in image memory 20.

Ultrasound apparatus 3 of the present embodiment further comprises in control unit 24:

color information acquisition means 93 for obtaining color information of the respective pixels in the thickness direction of the blood vessel wall in a color Doppler image being read out from image memory 20; and detecting means 94 for detecting inner wall 60 of tunica intima 42 that is the boundary between lumen 40 and tunica intima 42 based on color information outputted from color information acquisition means 93 and for outputting the detected boundary to calculation means 30. Color information acquisition means 93 and detection means 94 are installed in control unit 24 as a program containing the description of commands.

Figure 12:
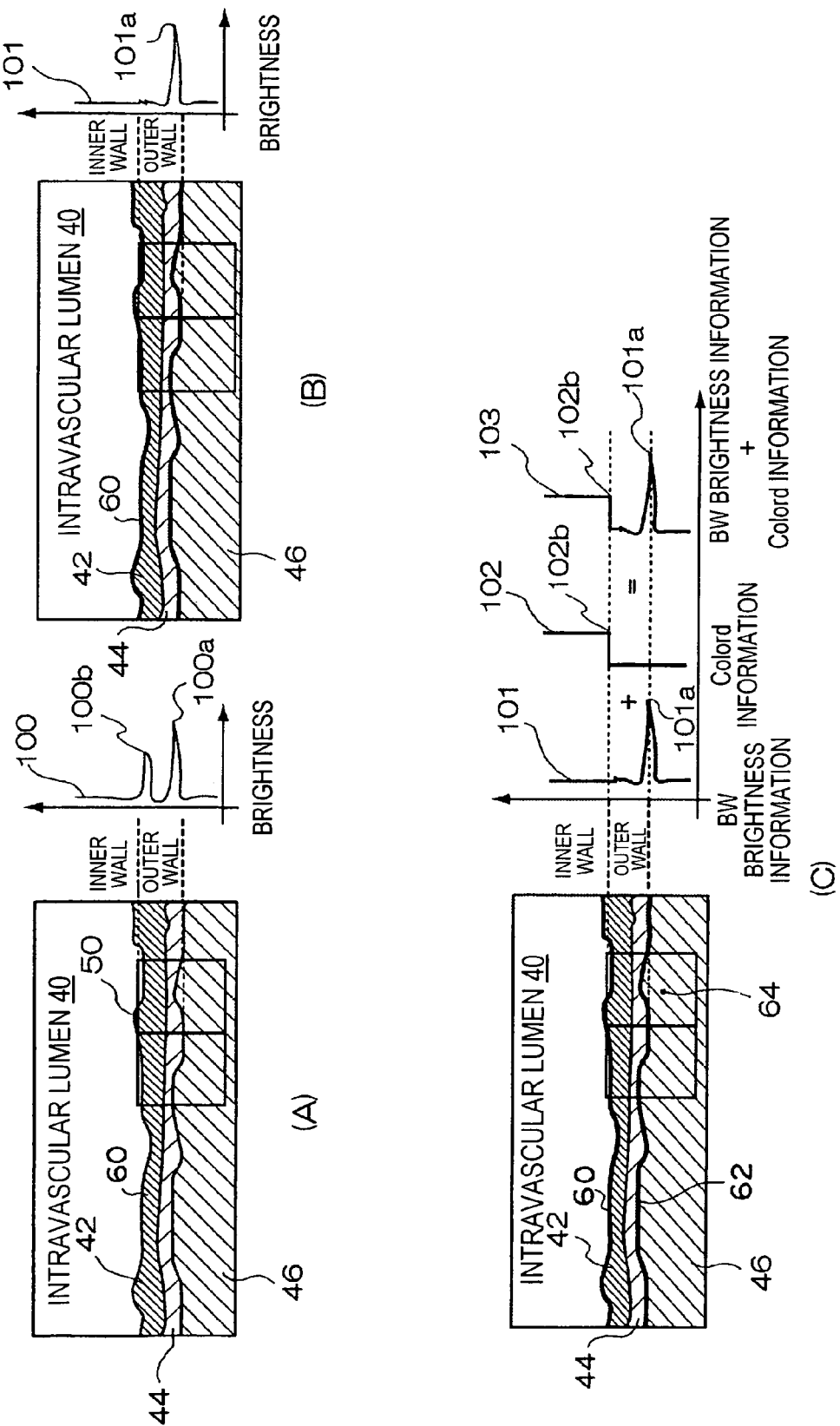
FIG. 12 is the ultrasonic images showing the cross-sectional view of a blood vessel wall of the carotid artery in the thickness direction in the sixth embodiment, and the brightness distribution lines in the thickness direction of a blood vessel wall.
Figure 13:
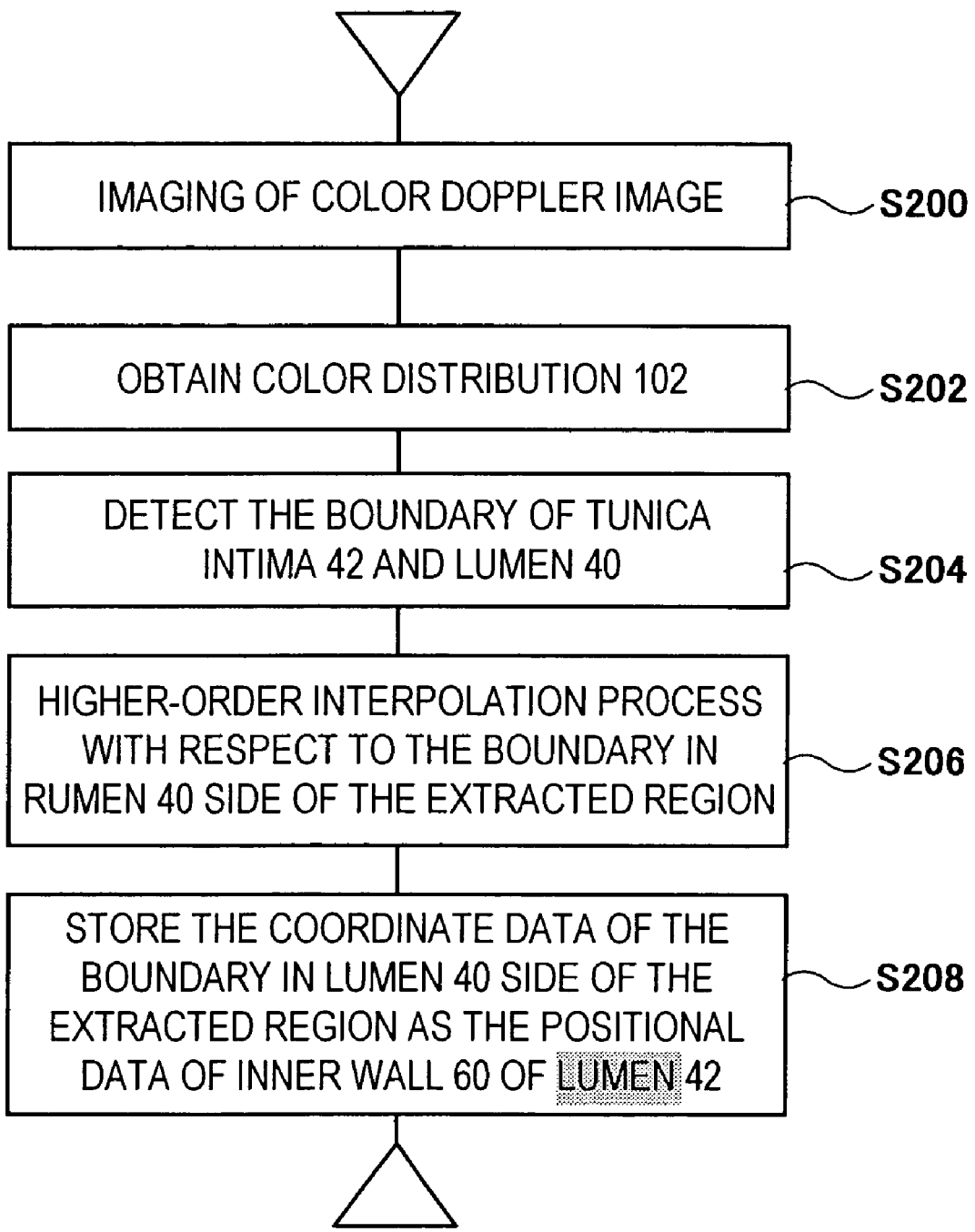
FIG. 13 is a flow chart indicating the process for obtaining the inner wall of the tunica intima in the sixth embodiment.

FIG. 12 shows the ultrasonic images illustrating the cross sectional view of carotid artery in the thickness direction of a blood vessel and the brightness distribution lines in the thickness direction of the blood vessel wall. FIG. 12 (A) is a tomogram to which processes S102 and S104 of FIG. 3 are carried out, and brightness distribution line 100 obtained by implementing process S106 in relation to the tomogram. Brightness distribution line 100 denotes the brightness distribution in the thickness direction of the far wall. In brightness distribution line 100 in FIG. 12 (A), as in the case in FIG. 2, local maximal point 100a having the maximum brightness and local maximal point 100b positioned on the side of lumen 40 from the position of local maximal point 100a appear clearly.

FIG. 12 (B) illustrates a tomogram to which the same process as FIG. 12 (A) is carried out, and a brightness distribution line. Brightness distribution line 101a in FIG. 12 (B) shows that local maximal point 101a having the maximum brightness appears clearly as in FIG. 12 (A). However as shown in FIG. 12 (B), the local maximal point positioned on the side of lumen 40 from the position of local maximal point 100a is does not appear clearly due to factors such as noise. Therefore in the case of FIG. 12 (B), there are occasions that the coordinate data of the boundary between lumen 40 and tunica intima 42 cannot be obtained. In terms of this, according to the present embodiment, the coordinate data of the boundary between lumen 40 and tunica intima 42 can be accurately detected regardless of the local maximal points on the side of lumen 40 not appearing clearly, based on the Doppler signals of the reflected echo signals generated from the object.

FIG. 12 (C) is a diagram for illustrating the process of the present embodiment. FIG. 13 is a flow chart for illustrating the process of the present embodiment. As for the process of the present embodiment, it may be carried out either via console 32 upon receiving a command to be executed, or automatically when the local maximal point appearing on the side of lumen 40 is smaller than the preset value.

First, the imaging of the color Doppler image is carried out (S200). For example, the reflected echo signals being outputted from phase addition unit 16 are imputed to image reconstruction unit 18 and Doppler calculation unit 91. Based on the inputted reflected echo signals, Doppler signals in relation to blood flow are detected by Doppler calculation unit 91. From the detected Doppler signals, for example, the average frequency or dispersion is obtained. According to the obtained average frequency or dispersion, color Doppler images are reconstructed by color mapping executed by Doppler image construction unit 92. The reconstructed color Doppler image is stored in image memory 20. The stored color Doppler image, according to the command of controller 24, is displayed on display unit 22 after being read out from image memory 20. The displayed color Doppler image of blood flow that is flowing toward probe 10 is displayed, for example, in red-end color and the one flowing away from probe 10 is displayed, for example, in blue-end color. That is, only the image region equivalent to lumen 40 with blood flow is color-displayed, and the region without blood flow (for example, tunica intima 42) is displayed in black and white.

Next, color distribution 102 in the thickness direction of a blood vessel is obtained (S202). For example, color distribution 102 in the thickness direction of a blood vessel is obtained by color information acquisition means 93 in relation to the color Doppler image read out from image memory 20. The obtained color distribution line 102 is a binarized chart, as shown in FIG. 12 (C), indicating "10" in relation to the coordinate of pixels in color, and "1" in relation to the coordinate of pixels in black and white.

Next, the boundary of lumen 40 and tunica intima 42 is detected (S204). For example, color distribution 102 obtained in the process of S202 is outputted to detection means 94.

Detection means 94 detects point 103 wherein the value of color distribution 102 intergrades, as the boundary between lumen 40 and tunica intima 42 (the inner wall of tunica intima 42). By such process being carried out repeatedly in the blood flow direction (lateral direction), the acquisition of the boundary between lumen 40 and tunica intima 42 is performed.

Next, the interpolation process is implemented on the boundary between lumen 40 and tunica intima 42 (S206). For example, the boundary detected by performing process of S204 is obtained in pixel units. Therefore, by implementing an interpolation process such as the least squares method or approximated curve in relation to the coordinate data of the respective pixels corresponding to the boundary, as in the same manner of S114 in FIG. 3, the coordinate data of the boundary becomes smooth. The interpolated coordinate data is stored as the positional data of tunica intima 42 and lumen 40 (S208). The buffer region provided in controller 24 is used as the storage region of the positional data.

According to the present embodiment, the positional data of the boundary between lumen 40 and tunica intima 42 (the inner wall of tunica intima 42) can be accurately detected based on the Doppler signals of the reflected echo signals generated from the object, regardless of the local maximal point appearing on the side of lumen 40 being unclear. And as in the same manner in the first embodiment, local maximal point 101a of brightness distribution line 101 is set as tunica externa SP64. The positional data of the inner wall 62 of tunica externa 46 is detected by executing the same process as FIG. 5 based on tunica externa SP64. IMT measurement is performed, by using calculating means 30 and calculating the distance, which is detected as described above, between inner wall 60 of tunica intima 42 and inner wall 62 of tunica externa 46.

The respective positional data of inner wall 60 of tunica intima 42 and inner wall 62 of tunica externa 46 may also be obtained based on composite line 103 which is created by combining brightness distribution line 101 and color distribution 102 in FIG. 12 (c). By displaying composite line 103 on display unit 22, inner wall 60 of tunica intima 42 and tunica externa SP64 can be visually recognized.

The following are additional descriptions of process S204. Color Doppler images are the images by which the respective pixels are color displayed based on RGB information. As for a pixel in the color display region of such color Doppler image, since the brightness ratio of RGB information is varied, for example, as R:G:B=103:30:10 (=13:3:1), the integration value of RGB information turns out to be "39". On the other hand, as for the pixel in the black and white display region of the color Doppler image, the brightness ratio of RGB information is, for example, R:G:B=1:1:1, and the integration value turns out to be "1". Therefore, the binarized chart illustrated in FIG. 12 (C) can be created, by setting, for example, "10" for color distribution 102 when the RGB integration value of the respective pixels is "1", and setting, for example, "1" for color distribution 102 when the integration value is "other than 1".

Instead of such binarization process, the integration value of RGB information may be obtained on the respective pixels, and, for example, "10" is set for color distribution 102 when the obtained integration value is over the threshold value of (for example, "5"), then, for example, "1" is set for color distribution 102 when the integration value is less than the threshold value. While an example of creating a binarized chart as shown in FIG. 12 (C) was illustrated for the convenience of description, it also is fine to create only a binarized table.

Also, in place of color Doppler images, power Doppler images for color displaying corresponding to the integration value of Doppler spectrum which is calculated based on the reflected echo signals outputted from phase addition unit 16 can be constructed.

The Seventh Embodiment

The seventh embodiment of the ultrasound diagnostic apparatus to which the present invention is applied as a medical imaging diagnostic apparatus will now be described referring to FIG. 14. In this embodiment, apparatuses such as an ultrasound diagnostic apparatus (real time) using a 2-dimensional array probe (not shown in the diagram), multi-slice CT or MRI are applied. It is for performing IMT measurement on the 3-dimensional image, by extracting a 3-dimensional region of a 3-dimensional image being obtained by the above-mentioned apparatuses such as ultrasound diagnostic apparatus, multi-slice CT or MRI.

In concrete terms, a 3-dimensional image is obtained and the 2-dimensional slice plane of the 3-dimensional image thereof as shown in FIG. 2 is displayed. Then in the same manner as the first embodiment, tunica intima SP54 and tunica externa SP64 are set in relation to this 2-dimensional slice plane. And the 3-dimensional region is extracted from the 3-dimensional image with each SP as a reference point. More precisely, extraction means 28 sets one point within the region of interest of the 3-dimensional image as reference point (x,y,z), and implements the setting of the threshold or the width of the threshold so that the width of the pixel value within the region can be indicated. For example, in relation to pixel value "n'" of the reference point displayed on display unit 22, the width "m'" is set (n' and m' are discretional integers). Thus the threshold width is given as "n'±m'", the lower limit threshold is given as "n'−m'" and the upper limit threshold as "n'+m'". Controller 24 detects the surrounding pixels of the reference point, and connects the regions having the pixel value within the threshold range in a 3-dimensional image. Ultimately the 3-dimensional region having the pixel value within the threshold range including the reference point can be obtained.

Figure 14:
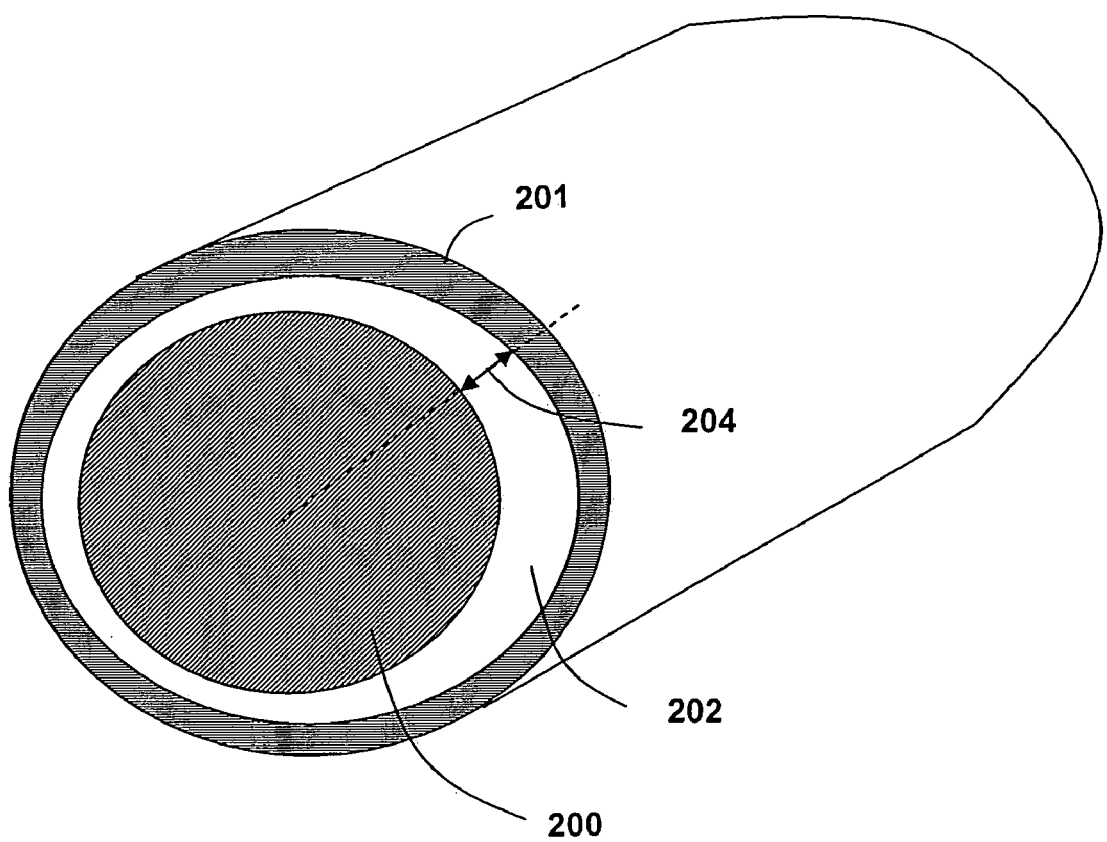
FIG. 14 is a diagram showing the seventh embodiment of the present invention.

Such an obtained 3-dimensional region is shown in FIG. 14, region 200 is lumen region (blood flow region), region 201 is tunica externa region and region 202 is tunica intima+tunica media regions. Using region 202 of this 3-dimensional region, IMT measurement is performed. In concrete terms, the inner wall position of the tunica intima and the inner wall position of tunica externa in a 3-dimensioanal region are extracted, and IMT is measured based on the distance between the point where the normal line of inner wall 60 of tunica intima 42 meets inner wall 62 of tunica externa 46 and the point of inner wall 60 of tunica intima 42. Also by emanating a line from the central point of the blood vessel cross-section, distance 204 between the intersecting points of inner wall 60 of tunica intima 42 and inner wall 62 of tunica externa 46 to the line may be measured. In this way by performing IMT measurement on all of the 3-dimensional regions, the measurement of IMT average value, maximum value and minimum value in these regions and the 3-dimensional positional information of these measurement values are outputted on the screen.

Therefore, even in the cases that the thickness of the tunica intima+tunica media vary in a cross section of the blood vessel, those cases can be accommodated properly. Also, when the IMT measurement value is topically abnormal, it is easy to find.

While the present invention had been described based on the first~seventh embodiments, it should not be taken as limited to the description. For example, although the region growing method was used for the examples of the region extracting method in the first~third and the seventh embodiments, other methods such as block matching method, SAD method and edge extraction method can be used to extract the boundary between the lumen and the tunica intima, or the tunica media and the tunica externa.

The invention claimed is:

1. A medical imaging diagnostic apparatus that obtains image data from a blood vessel of an object being examined and measures the composite thickness of a tunica intima and a tunica media of the blood vessel, comprising:
    brightness distribution acquisition means for acquiring a brightness distribution in the thickness direction of a blood vessel wall in a tomogram with regard to the blood vessel,
    setting means for setting the tunica intima reference point and the tunica externa reference point based on the brightness distribution,
    extraction means for extracting pixels, with respect to each pixel in a setting range including the tunica intima reference point or the tunica externa reference point, wherein the brightness belongs to the setting range, and
    calculation means for calculating first boundary in the lumen side between an intravascular lumen and an end of a region formed by the pixels being extracted, calculating a second boundary in the lumen side in a region formed by the pixels being extracted based on the tunica externa reference point, and calculating a distance between the first boundary and the second boundary by interpolating the composite thickness of the tunica intima and the tunica media.

2. The medical imaging diagnostic apparatus according to claim 1, comprising means to make the threshold value variable.

3. The medical imaging diagnostic apparatus according to claim 1, wherein:
    the setting means sets a first region of interest in the position equivalent to the lumen, and sets a brightness difference between an average brightness within the first region of interest and the brightness of the tunica intima reference point as a threshold, and
    the extraction means extracts the tunica intima reference point based on the set threshold.

4. The medical imaging diagnostic apparatus according to claim 3, wherein the extraction means determines that the pixels having the brightness, when the absolute value of the brightness difference is smaller than the threshold value, are equivalent to a tunica intima.

5. The medical imaging diagnostic apparatus according to claim 1, wherein a plurality of brightness distribution lines running in the diameter direction of the blood vessel over in the blood flow direction are obtained and the tunica intima reference point is set based on the average brightness distribution line of the obtained respective distribution lines.

6. The medical imaging diagnostic apparatus according to claim 1, wherein a local maximal point closest to the lumen side, from the local maximal point previously set as the tunica intima reference point, is reset as a tunica intima reference point.

7. The medical imaging diagnostic apparatus according to claim 1, wherein the tunica intima is obtained based on a color distribution of Doppler signals of reflected echo signals.

8. The medical imaging diagnostic apparatus according to claim 7, wherein a binarization process is implemented, and the tunica intima is obtained based on the result of the binarization process.

9. The medical imaging diagnostic apparatus according to claim 1, wherein the setting means sets the coordinate of a point having the maximum brightness value in relation to the brightness distribution in the thickness direction as a tunica externa reference point.

10. The medical imaging diagnostic apparatus according to claim 9, wherein:
    the setting means sets a second region of interest between the tunica intima reference point and the tunica externa reference point, and a brightness difference between an average brightness within the second region of interest and the brightness of the tunica externa reference point as the threshold value, and;
    the extraction means extracts the tunica externa based on the set threshold value.

11. The medical imaging diagnostic apparatus according to claim 1, comprising signal processing means having a filter for emphasizing the contour of the pixel region being extracted by the extraction means.

12. The medical imaging diagnostic apparatus according to claim 1, wherein:
    the extracted pixels correspond to 3-dimensional image data, and
    the extraction means extracts the tunica intima and the tunica externa on the 3-dimensional region, and measures the composite thickness of the tunica intima and a tunica media.

13. The medical imaging diagnostic apparatus according to claim 1, comprising:
    a probe for transmitting/receiving ultrasonic waves to/from an object being examined;
    a transmission/reception unit for providing driving signals to the probe and receiving the reflected echo signals;
    an image construction unit for reconstructing ultrasound images based on the reflected echo signals; and
    a display unit for displaying the ultrasonic images,
    wherein the image data is the ultrasound image data obtained by transmitting/receiving ultrasonic waves to/from the object.

14. The medical imaging diagnostic apparatus according to claim 13, wherein a blood vessel wall on the side near the probe is set as a near wall and a blood vessel wall on the side far from the probe as a far wall, the measured value of the near wall and far wall are compared to each other, and the greater value thereof is set as the measurement value of the cross section.

15. The medical imaging diagnostic apparatus according to claim 1, wherein the calculation means calculates the average value of the measured value in the region being extracted based on the extracted region.

16. The medical imaging diagnostic apparatus according to claim 1, comprising:
    a display unit for displaying the calculated value,
    wherein the calculating means calculates a maximum value or a minimum value in the extracted region, and
    wherein the location of the maximum value or the minimum value in the extracted region is marked on the display unit.

17. The medical imaging diagnostic apparatus according to claim 1, comprising:
    display means for displaying the composite thickness of the tunica intima and tunica media of the blood vessel based on the distance.

18. A medical imaging diagnostic apparatus comprising:
imaging means for obtaining image data related to a blood vessel of an object being examined;
Doppler imaging means for obtaining color Doppler image data related to the blood vessel;
brightness distribution acquisition means for acquiring the brightness distribution in the thickness direction of the blood vessel wall of the color Doppler image data;
setting means for setting the tunica intima reference point and the tunica externa reference point based on the brightness distribution;
extraction means for extracting the pixels, with respect to each pixel in the setting range including the tunica intima reference point or the tunica externa reference point, wherein the brightness belongs to the setting range; and
calculating means for calculating a first boundary in the lumen side between an intravascular lumen and an end of a region formed by the pixels being extracted, calculating a second boundary in the lumen side in a region formed by the pixels being extracted based on the tunica externa reference point, and calculating a distance between the first boundary and the second boundary by interpolating the composite thickness of the tunica intima and the tunica media.

19. A medical imaging diagnostic method comprising:
acquiring a brightness distribution in the thickness direction of a blood vessel wall in a tomogram with regard to the blood vessel,
setting a tunica intima reference point and a tunica externa reference point based on the brightness distribution,
extracting pixels, with respect to each pixel in a setting range including the tunica intima reference point or the tunica externa reference point, wherein the brightness belongs to the setting range,
calculating a first boundary in the lumen side between an intravascular lumen and an end of a region formed by the pixels being extracted,
calculating a second boundary in the lumen side in a region formed by the pixels being extracted based on the tunica externa reference point, and
calculating a distance between the first boundary and the second boundary by interpolating the composite thickness of the tunica intima and the tunica media.

* * * * *